United States Patent

Näfe et al.

[11] Patent Number: 5,954,930
[45] Date of Patent: Sep. 21, 1999

[54] REFERENCE ELECTRODE FOR ELECTROLYTIC CELLS HAVING AN ION-CONDUCTING SOLID ELECTROLYTE

[75] Inventors: Helfried Näfe; Carsten Schwandt, both of Stuttgart; Martin Schmäh, Frankfurt, all of Germany

[73] Assignee: Max-Planck-Gesellschaft Zur Förderung Der Wissenschaften, München, Germany

[21] Appl. No.: 09/137,182

[22] Filed: Aug. 20, 1998

Related U.S. Application Data

[63] Continuation of application No. 08/687,505, filed as application No. PCT/EP95/00454, Feb. 8, 1995, abandoned.

[30] Foreign Application Priority Data

Feb. 8, 1994 [DE] Germany .......................... P 44 03 909

[51] Int. Cl.[6] .................................................. G01N 27/407
[52] U.S. Cl. ........................ 204/421; 204/424; 204/426; 204/435; 205/781; 205/784; 205/786.5
[58] Field of Search ............................ 204/435, 421–429; 205/783.5, 784, 784.5, 785

[56] References Cited

U.S. PATENT DOCUMENTS 3,914,169 10/1975 Horowitz ................................ 204/427
4,199,424 4/1980 Teitelbaum ............................. 204/428

FOREIGN PATENT DOCUMENTS 4112301 10/1992 Germany .

OTHER PUBLICATIONS

Maruyama et al, "Potentiometric Gas Sensor for Carbon Dioxide Using Solid Electrolytes", Solid State Ionics, vol. 23, pp. 107–112 (1987) Month unavailable.

*Primary Examiner*—T. Tung
*Attorney, Agent, or Firm*—Fulbright & Jaworski, LLP

[57] ABSTRACT

The invention relates to a reference electrode for electrolytic cells having an ion-conducting solid electrolyte, to sensors comprising the reference electrode of the invention and to their use of the reference electrode for analyzing gases.

13 Claims, 5 Drawing Sheets

REFERENCE ELECTRODE FOR ELECTROLYTIC CELLS HAVING AN ION-CONDUCTING SOLID ELECTROLYTE

This application is a continuation of U.S. Ser. No. 08/687,505 filed Jul. 29, 1996, now abandoned which is a 371 of EP95/00454 Feb. 8, 1995.

This invention relates to a reference electrode for electrolytic cells having an ion-conducting solid electrolyte, to sensors comprising the reference electrode of the invention and to their use of the reference electrode for analyzing gases.

The use of electrolytic cells having a solid electrolyte as gas sensors, especially as oxygen sensors, has been known for a long time. Sensors for analyzing other gases, however, have so far been almost impossible to obtain commercially. This is due mainly to the fact that it is comparatively more difficult to realize reference electrodes of practical applicability. The use of cation-conducting solid electrolytes, for example a sodium ion conductor, necessitates maintaining a defined sodium potential over long periods of time. According to prior art, this is still best achieved by making use of metallic sodium, which is liquid and highly reactive at the operating temperatures—frequently above 500° C.—of the sensor. The construction of such an electrode thus involves substantial difficulties, namely in insulating the electrode spaces hermetically from one another and from the surroundings. Reactions of the molten sodium with the insulating material or with other components of the electrolytic cell result in the sensor signal being impaired or in the sensor being totally destroyed with time.

In the DE-A-41 12 301.8 the alternative use of a reference electrode is suggested which contains an alkali metal compound, in particular a sodium compound in multinary multi-phase equilibrium (e.g. binary Na/metal compounds or ternary Na/metal/oxide compounds). Examples of such reference electrodes having binary sodium/metal compounds are Na—Sb or Na—Bi, examples of such reference electrodes having ternary sodium/metal/oxide compounds are Na—Co-oxide or Na—Ni-oxide. However, on account of the toxicity of the heavy metal compounds used, production of these reference electrode systems is problematical.

It is also known that the metal activity brought about at the phase boundary between a solid electrolyte and a precious metal adhering thereto fulfils the function of a reference system (cf. Saito and Maruyama, Solid State Ionics 28–30 (1988), 1644). Here there is often the danger, however, that due to the inherently incomplete separation of reference and measuring electrodes the reference will react with the measuring medium, for example $CO_2$ and $O_2$. It is then only a matter of time until the cell voltage of a sensor of this type decreases to 0 and the reference electrode loses its functionality (cf. Maruyama et al., Solid State Ionics 23 (1987), 107).

In the literature source cited above (Solid State Ionics 23 (1987), 107), Maruyama et al., a $CO_2$ sensor is also suggested in which use is made of a combination of different solid electrolytes, namely of an oxygen-ion and of a sodium-ion conductor. The reference electrode here is the $Na_2O$ formed at the phase boundary between the two solid electrolytes once these have been sintered together. It has been shown that the potential of this reference electrode responds more than would be expected to changes in the partial pressure of oxygen in the surrounding atmosphere. This means that the cell voltage of such a sensor is not stable in terms of time, and is accordingly not a clear function of $CO_2$ partial pressure.

One object of the present invention is to provide a reference electrode in which the above-mentioned disadvantages of the prior art are—at least in part—avoided, and which, in particular, guarantees permanent insulation of the reference electrode space from the surroundings, thus having greater long-term stability than known systems and being considerably easier to make.

This object is established according to the invention by provision of a reference electrode for electrolytic cells having an ion-conducting solid electrolyte and comprising a glass phase which is in contact with an electronically conductive phase and with said ion-conducting solid electrolyte and in which the species for which the solid electrolyte is conductive is dissolved, the glass phase bringing about activity of this species which activity is only dependent on the temperature and is stable in terms of time, and simultaneously being used for hermetically insulating the reference electrode space from the surroundings.

The term "glass phase" is used in this invention to mean a highly viscous phase of predominantly amorphous structure, which contains simple and/or complex phosphates, silicates, borosilicates and/or borates as network formers and all sorts of different cations (alkali, alkaline earth metals etc.) as network modifiers. On fusing of the glass phase further species dissolve therein which, together with the glass as solvent, form a highly viscous solution. The term "species" as used in this context includes in particular atoms and chemical compounds which are dissolved in the glass in predominantly covalent or ionogenic form and which, by way of corresponding dynamic equilibria, determine the potential of the reference electrode in question.

The glass phase of the reference electrode of the invention is advantageously of a composition that does not impair the functionality of the reference electrode by way of chemical and/or physical changes during the production and use of said electrode. It is particularly important that if the reference electrode has a cation-conducting solid electrolyte, e.g. an alkali-metal-ion-conducting solid electrolyte, the glass phase should not contain any components which are reducible on contact with the solid electrolyte under the conditions prevailing during fusing and during operation of the reference electrode.

If the glass phase of the reference electrode is a borate glass, it is advantageous if it comprises an oxide mixture with the following nominal composition:

0 to 20 wt. % $Al_2O_3$,
18 to 30 wt. % $B_2O_3$,
36 to 53 wt. % BaO,
15 to 20 wt. % CaO and
0 to 15 wt. % $Na_2O$, with the proportion of $B_2O_3$ plus $Al_2O_3$ being within the range from 28 to 40 wt. %. It is especially preferable if the glass phase comprises an oxide mixture with the following nominal composition:

36 to 46 wt. % BaO,
18 to 20 wt. % CaO.
15 to 20 wt. % $Al_2O_3$,
15 to 22 wt. % $B_2O_3$ and
0 to 5 wt. % $Na_2O$.

The glass phase should have a melting range which allows fusing without irreversible changes occurring in the other components of the sensor at the temperatures required therefor, but which, despite this, also guarantees that the species for which the solid electrolyte is conductive dissolves in the glass phase in a reasonable amount of time and in a sufficient quantity. It is a further advantage if the glass phase has a coefficient of expansion which largely matches that of the solid electrolyte material.

In a special embodiment of the invention the glass phase of the reference electrode can be made up of two different nominal compositions which are distinguished by having different melting ranges and thus different degrees of viscosity at the operating temperature. In this case the composition with the lower melting range is directly in contact with the ion-conducting solid electrolyte and is insulated additionally from the surroundings by a layer of glass having the second composition.

The invention is now explained in detail by reference to FIGS. 1 to 5.

In a first embodiment of the invention the ion-conducting solid electrolyte is an oxygen-ion conductor and the electronically conductive phase a metal which under the reference electrode production conditions, is superficially oxidizable with the oxide layer dissolving at least partially in the glass phase during fusing thereof. The oxide layer of the metal used should not be reducible under the conditions prevailing during preparation of the reference electrode. Examples of suitable metals are iron, cobalt, nickel, manganese or an alloy based on one or several of these metals.

The oxygen-ion conducting solid electrolyte can, for example, be a material based on $ZrO_2$, $ThO_2$, $CeO_2$, $HfO_2$ or $Bi_2O_3$. A material particularly preferred as oxygen-ion-conducting solid electrolyte is one based on cubic, tetragonal or partially stabilized $ZrO_2$.

A reference electrode of this kind, having an oxygen-ion-conducting solid electrolyte, can be made for instance by fixing the solid electrolyte to a metal component by means of glass soldering, without additionally making use of a specially-made reference electrode system. The same effect is obtained by having the solid electrolyte, glass and metal disposed in superimposing layers. During the soldering process, the solder glass wets both the surface of the solid electrolyte and that of the metal, as a result of which—at the metal-glass phase boundary—the oxidic tarnish on the metal dissolves in the glass and the oxide dissolved in the glass, together with the metal, forms an equilibrium system between an oxidized and a reduced phase. In this way a hermetically insulated reference electrode space is provided using the simplest of means. The oxygen-ion-conducting solid electrolyte is preferably a cubically (e.g. $YO_{1.5}$) stabilized $ZrO_{2\ body}$. The measuring electrode takes the form of an electronically conductive coating (e.g. Pt) on the solid electrolyte surface which is in contact with the surroundings.

Figure 1:
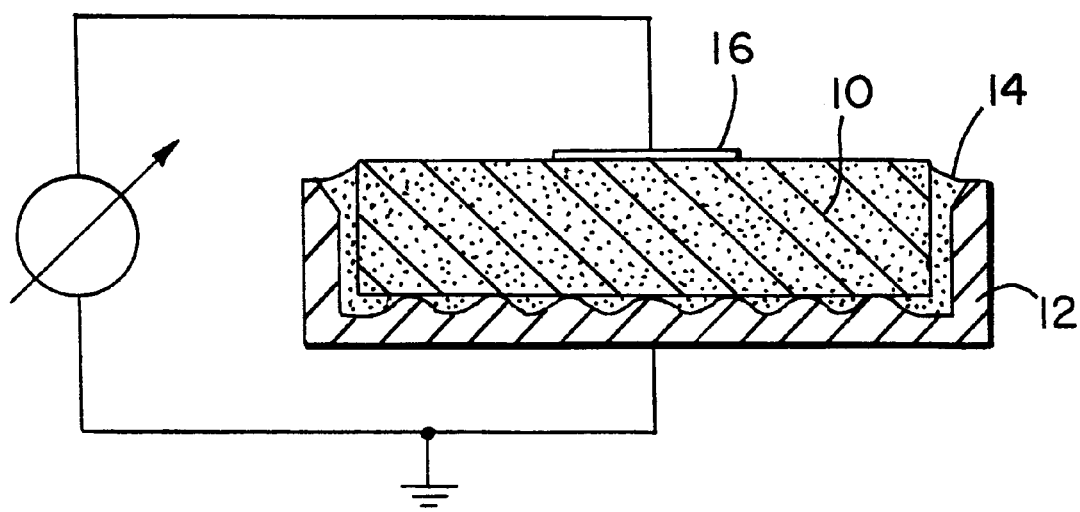
FIG. 1 shows a first embodiment of the reference electrode of the invention having an oxygen-ion-conducting solid electrolyte.

The basic assembly of this embodiment of the reference electrode according to the invention is shown exemplarily in FIG. 1. The oxygen-ion-conducting solid electrolyte (10), a pellet of $YO_{1.5}$—stabilized $ZrO_2$, for example, is disposed in an appropriately shaped metal body (12) for which use is made preferably of a Fe—Ni sealing alloy with a coefficient of expansion similar to that of $ZrO_2$ (e.g. FeNi48). Under particularly corrosive conditions use can be made instead, for instance, of nonscaling steel (e.g. X10CrAl13). It is of advantage if that portion of the surface of the metal body (12) that is in the soldering zone, i.e. is in contact with the glass phase, has been rendered slightly tarnished by means of heat treatment. In order to obtain a glass layer which is as thin as possible it is also of advantage if that portion of the metal surface which is in direct contact with the glass phase is textured, having shallow grooves. As solder use can be made e.g. of an oxide mixture (14) having the following composition: 41 wt. % BaO, 19 wt. % $Al_2O_3$, 19 wt. % CaO and 21 wt. % $B_2O_3$. This is painted thinly in the form of powder in an amyl acetate suspension onto the bottom of the metal cap and is introduced into the rest of the soldering recess. The oxide mixture is fused at approximately 1060° C. The electronically conductive phase of the reference electrode is formed by the metal component (12). The measuring electrode takes the form of an electronically conductive coating (16), e.g. of Pt, on the side of the solid electrolyte that is disposed towards the surroundings.

The potential of the reference electrode prepared in this way is directly proportional to temperature in the range from 350° C. to 500° C. The cell voltage against air is given by the equation:

$$U[mV]=-1401+0.490T-0.0215T\ln \rho_{O2}$$

where T is expressed in K and $\rho_{O2}$ in bar.

Figure 2:
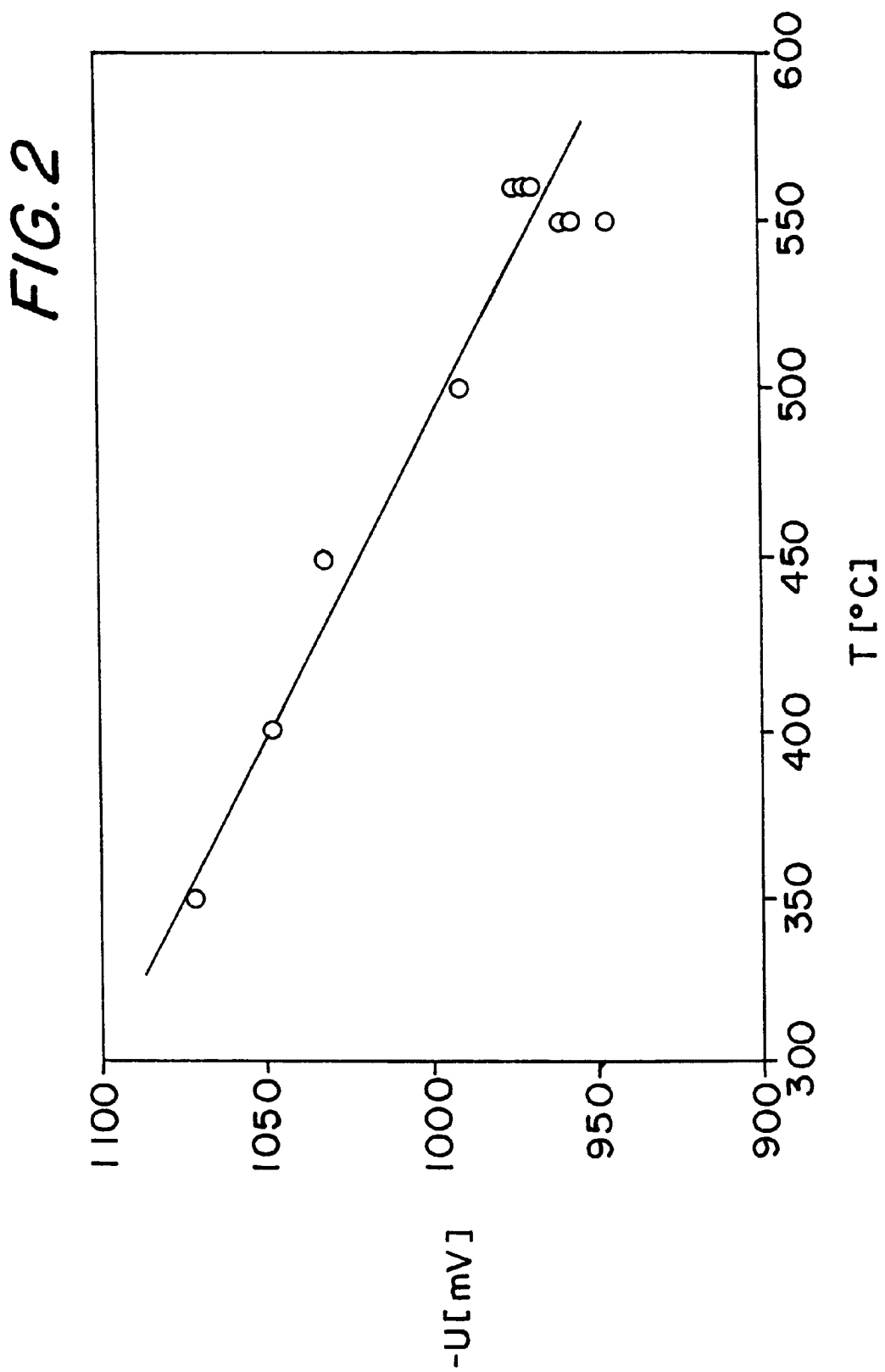
FIG. 2 shows the temperature dependency of the potential of the reference electrode of FIG. 1 against a $ZrO_2$/Pt, $O_2$ (0.2 bar) electrode.

FIG. 2 shows the temperature dependence of the cell voltage U[mV] set up between the reference electrode of the invention and a $ZrO_2$/Pt, $O_2$ (0.2 bar) electrode.

In a second embodiment of the present invention the ion-conducting solid electrolyte is a cation conductor and the glass phase brings about a metal activity by having a metal species dissolved in it. The cation-conducting solid electrolyte can, for instance, be a material based on beta-$Al_2O_3$, Nasicon or Lisicon. It is preferably an alkali metal ion conductor, e.g. a sodium, potassium or lithium ion conductor, with a sodium ion conductor such as Na—beta—$Al_2O_3$ being especially preferable.

The metal activity of the glass phase can be brought about by using a glass having a defined metal content, equilibrizing the glass phase during fusing with the adjoining layer of solid electrolyte or/and enriching the glass phase after it has been fused onto the solid electrolyte by means of coulometric titration with a metal species.

With a reference electrode according to the invention and having an alkali-metal-ion-conducting solid electrolyte it is advantageous if the glass phase is of a composition that does not include lead oxide in a quantity which lowers the viscosity of said glass phase. Lead oxide can be reduced when the reference electrode is in operation, thus leading to irreversible chemical and physical changes in the reference electrode. The glass phase preferably contains lead oxide in a quantity amounting to less than 10 wt. %, more preferably less than 5 wt. % and most preferably less than 1 wt. %.

The measuring electrode of a sensor having a cation-conducting, in particular an alkali-metal-ion-conducting solid electrolyte includes an electronically conductive material, preferably a layer of Au, on the solid electrolyte surface disposed towards the measuring medium. The electronically conductive material makes contact with a layer of a compound, e.g. $Na_2CO_3$ or $NaNO_3$, that coats the surface of the solid electrolyte, the cation of which compound is identical with the mobile ion of the solid electrolyte; the compound is in thermodynamic equilibrium with the gas to be measured, e.g. $CO_2$ and $O_2$. Accordingly, nitrates are used for the measurement of $NO_x$, ($N_2O$, NO, $NO_2$), sulfates for the measurement of $SO_x$ ($SO_2$, $SO_3$) and carbonates for the measurement of $CO_2$.

Figure 3:
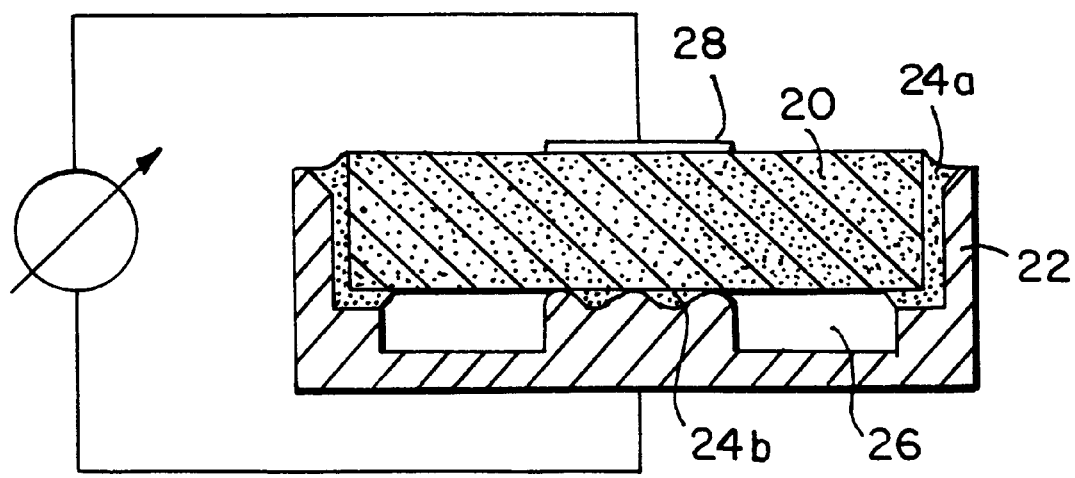
FIG. 3 shows a second embodiment of the reference electrode of the invention having a sodium-ion-conducting solid electrolyte.

The basic assembly of this embodiment of the reference electrode according to the invention is shown exemplarily in FIG. 3. The cation-conducting solid electrolyte (20), e.g. a pellet of Na—β"—$Al_2O_3$, is disposed in an appropriately shaped metal component, preferably a metal cap (22), for which use is made preferably of a sealing alloy (e.g. FeNi 48) or of nonscaling steel (e.g. X10CrAl13). Here too, a planar assembly is possible, with the materials used being superimposed upon each other in layers. As glass phase use is made, for example, of an oxide mixture having the following composition: 51 wt. % BaO, 10 wt. % $Al_2O_3$, 15 wt. % CaO, 22 wt. % $B_2O_3$ and 2 wt. % $Na_2O$. The glass phase (24a), which is in contact with the surroundings, can for instance be selected such that it has a melting range which is higher than that of the glass phase (24b) by, for example, 100–200° C., preferably by about 150° C. For said glass phase use can be made for instance of an oxide mixture having the following composition: 41 wt. % BaO, 19 wt. % $Al_2O_3$, 19 wt. % CaO, 21 wt. % $B_2O_3$. The glass phase can be painted thinly in the form of a powder in an amyl acetate suspension onto the bottom of the metal cap (22). The surface portion in contact with the glass phase (24b) is preferably separated from the rest of the soldering recess by means of a step (26) in the metal body and is textured with shallow grooves so that the glass layer can be kept as thin as possible. The oxide mixture is fused at a temperature between 900 and 1060° C.

The glass phase used (24b) can have a defined metal content, and/or the necessary amount of metal can be introduced by means of equilibrating it with the solid electrolyte. The glass phase can also be enriched with the metal species, e.g. sodium, by applying a voltage between the Au layer (28) and the metal cap (22), i.e. by means of coulometric titration.

Figure 4:
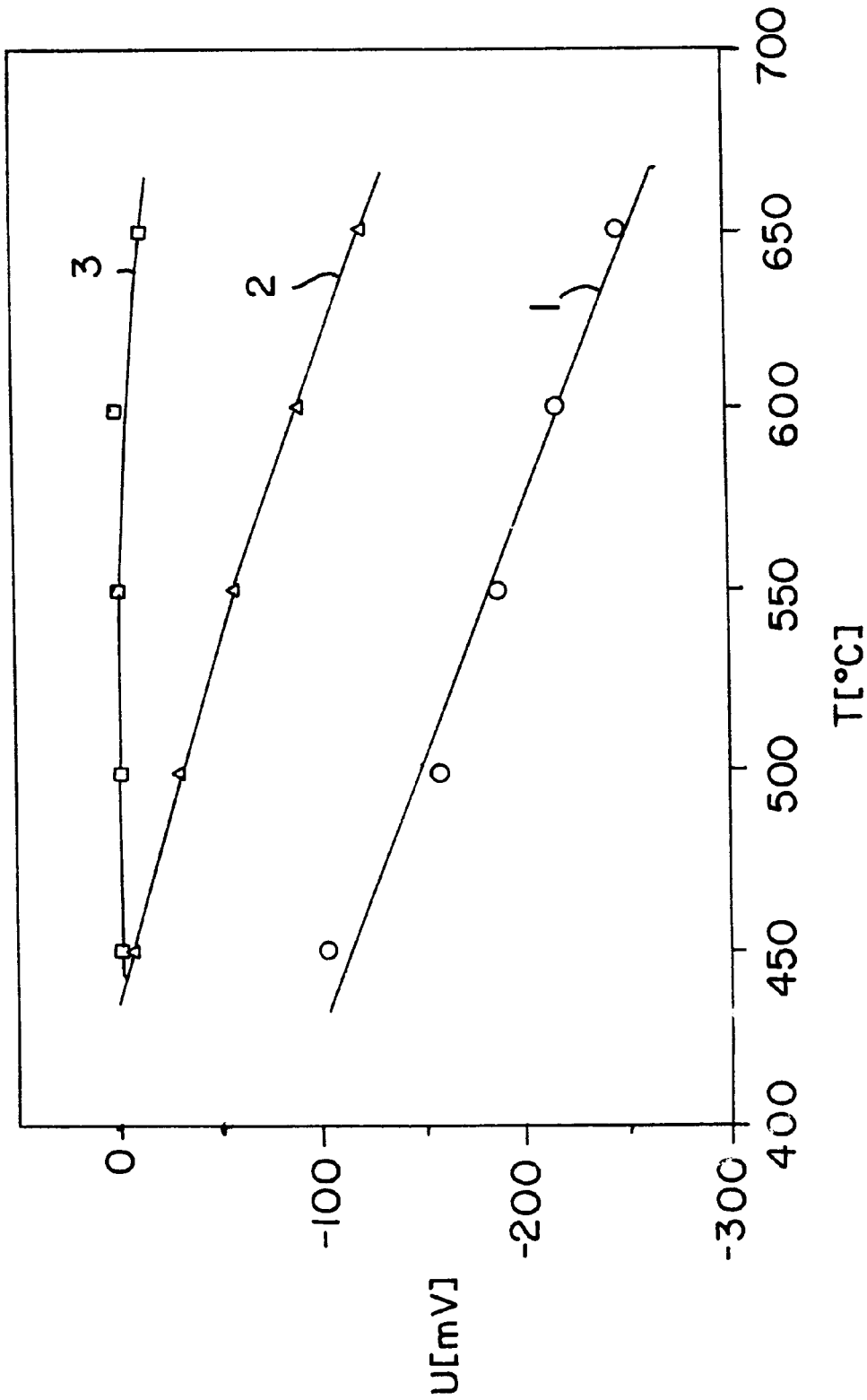
FIG. 4 shows the temperature dependency of the potential of the reference electrode of FIG. 3 against a $\beta''$—$Al_2O_3$/$Na_2CO_2$, Au, $CO_2$, $O_2$-electrode.

Against Na—β"—$Al_2O_3/Na_2CO_3$, Au, $CO_2$ ($P_{CO_2}$), $O_2$ ($P_{O_2}$) a reference electrode made in this way has a cell voltage with the temperature dependence shown in FIG. 4: (plot 1: $P_{CO_2}$=20.8 Pa, $P_{O_2}$=20.5 Pa; plot 2: $P_{CO_2}$=1 KPa, $P_{O_2}$=1 KPa; plot 3: $P_{CO_2}$=16.3 KPa, $P_{O_2}$=85 KPa).

A further subject of the present invention is a sensor, in particular a sensor for measuring gases, having at least one reference electrode according to the invention and at least one measuring electrode suitable for the particular sensor function. The measuring signal of the sensor is brought about by a potential difference between reference and measuring electrode, said potential difference being proportional to the partial pressure of the gases to be measured, in particular $O_2$, $NO_x$ ($N_2O$, NO and $NO_2$), $SO_x$ ($SO_2$, $SO_3$) or $CO_2$.

The sensor of the invention preferably contains a combination of two different reference electrode/solid electrolyte/measuring electrode arrangements. If a combination of an oxygen-ion- and a cation-conducting solid electrolyte is used, the resulting sensor provides a measuring signal which is independent of the partial pressure of the oxygen in the measuring medium. It is preferable here if the two measuring electrodes of the sensor according to the invention are in contact with measuring media in which the partial pressure of oxygen is more or less the same. It is especially preferable if the two measuring electrodes are in contact with the same measuring medium.

It is also of advantage if the two reference electrodes form a reference electrode space which is at least in part common to both electrodes and which connects the two solid electrolytes of the sensor electrically with each other.

Sensors of this kind are of particular interest for detecting $CO_2$, $NO_x$ or $SO_x$, both in trace amounts and at higher concentrations.

In this embodiment of the present invention the glass phases in contact with the respective solid electrolytes are electrically interconnected, for example by means of a common electronically conductive phase. Alternatively, use can also be made of a common glass phase having simultaneously a defined alkali metal and oxygen activity.

Figure 5:
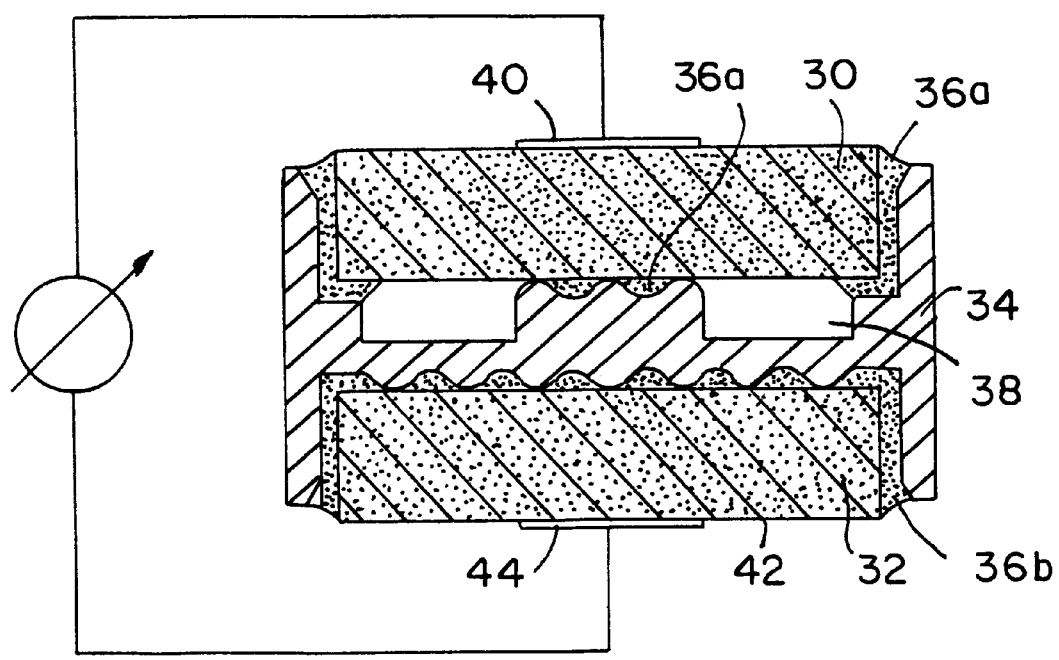
FIG. 5 shows a third embodiment of the reference electrode of the invention having a combination of an oxygen-ion-conducting and a sodium-ion-conducting solid electrolyte.

The basic assembly of an embodiment of a sensor having two reference electrodes is shown exemplarily in FIG. 5. The two solid electrolytes, pellets of Na—β"—$Al_2O_3$ (30) and cubically (e.g. $YO_{1.5}$)—stabilized $ZrO_2$ (32), are disposed in an appropriately shaped metal component (34) which is preferably designed as a cap and which consists of nonscaling steel (e.g. X10CrAl13); here too, a planar assembly is possible. As glass phase (36a, 36b) use can be made of an oxide mixture having, for example, the following composition: 41 wt. % BaO, 19 wt. % $Al_2O_3$, 19 wt. % CaO and 21 wt. % $B_2O_3$. The oxide mixture is painted in the form of a powder in an amyl acetate suspension onto the two solid electrolyte contact surfaces and is subsequently introduced into the other soldering recesses. So that the glass layer can be kept as thin as possible, the surface of the metal body (34) is textured by means of shallow grooves in the areas which are in direct contact with the solid electrolytes. The surface area disposed towards the alkali-metal-ion-conducting solid electrolyte (30) also has a step (38) which interrupts the glass phase (36a). The glass phase (36a) can—as described in the explanation of FIG. 3—consist of a component with a higher melting range and a component with a lower melting range. The glass is fused by applying a small amount of pressure to the two solid electrolyte pellets. After a layer of gold has been vapour-deposited on an area (40) of the measuring-electrode-side of the sodium-ion-conducting solid electrolyte, a thin layer of a sodium salt (e.g. $NaNO_3$, $Na_2CO_3$ or $Na_2SO_4$) is deposited on the latter. A Pt coating (44) is applied to part of that surface (42) of the oxygen-ion-conducting solid electrolyte (32) that is disposed towards the surroundings. The cell voltage between the Au/$Na_2CO_3$/β"—$Al_2O_3$ electrode and the Pt/$YO_{1.5}$—stabilized $ZrO_2$ electrode is measured.

We claim:

1. An electrolytic cell comprising:
   a glass phase;
   an electronically conductive phase comprising a metal, wherein said electronically conductive phase is in contact with the glass phase; and
   an ion-conducting solid electrolyte which is conductive for a species, said solid electrolyte being in contact with the glass phase;
   the glass phase having dissolved therein the species for which the solid electrolyte is conductive,
   wherein a reference electrode is provided by contact of said glass phase with said electronically conductive phase and said ion-conducting electrolyte, and
   wherein the glass phase comprises an oxide of the metal of the electronically conductive phase and brings about activity of said species, said activity being dependent only on the temperature and being stable in terms of time, and said glass phase hermetically insulating the reference electrode from the surroundings.

2. An electrolytic cell according to claim 1,
   wherein
   The glass plate is of a composition that does not impair the functionality of the reference electrode by way of chemical or physical changes during the production and use of the electrode.

3. An electrolytic cell according to claim 1, wherein
the glass phase is an oxide mixture having the composition
0 to 20 wt. % $Al_2O_3$,
18 to 30 wt. % $B_2O_3$,
36 to 53 wt. % BaO,
15 to 20 wt. % CaO and
0 to 15 wt. % $Na_2O$
with the percentage of $B_2O_3$ plus $Al_2O_3$ being within the range from 28 to 40 wt.-%.

4. An electrolytic cell according to claim 1, wherein said glass phase has expansion characteristics which largely match in particular those of said solid electrolyte.

5. An electrolytic cell according to claim 1, wherein the ion-conducting solid electrolyte is an oxygen-ion conductor and the electronically conductive phase is a metal which, under the reference electrode production conditions, is superficially oxidizable with an oxide layer dissolving at least partially in the glass phase.

6. An electrolytic cell according to claim 5 wherein the metal is selected from the group consisting of iron, cobalt, nickel and manganese or wherein said metal is an alloy based on one or more of said group.

7. An electrolytic cell according to claim 1 wherein the oxygen-ion-conducting solid electrolyte is a material based on one of the group consisting of $ZrO_2$, $ThO_2$, $CeO_2$, $HFO_2$ and $Bi_2O_3$.

8. An electrolytic cell according to claim 1, wherein the ion-conducting solid electrolyte is a cation conductor and the glass phase brings about a metal activity by having metal species dissolved therein.

9. An electrolytic cell according to claim 8, wherein the ion-conducting solid electrolyte is an alkali-metal-ion conductor and the glass phase brings about an alkali metal activity by having alkali metal species dissolved therein.

10. An electrolytic cell according to claim 8, wherein the cation-conducting solid electrolyte is a material comprising at least one member selected from the groups consisting of beta-$Al_2O_3$, Nasicon and Lisicon.

11. An electrolytic cell according to claim 8, wherein the cation-conducting solid electrolyte is a sodium ion conductor.

12. An electrolytic cell according to claim 8, wherein the metal activity of the glass phase is realized by using a glass with a defined metal content or by creating equilibrium of the glass phase during fusing with an adjoining layer of solid electrolyte or/and enriching the glass phase after it has been fused onto the solid electrolyte by means of coulometric titration with a metal species.

13. An electrolytic cell according to claim 8, wherein the glass phase is of a composition that does not include lead oxide in a quantity which lowers the viscosity.

* * * * *

UNITED STATES PATENT AND TRADEMARK OFFICE
CERTIFICATE OF CORRECTION

PATENT NO. : 5,954,930
DATED : Sep. 21, 1999
INVENTOR(S) : Nafe, et al.

It is certified that error appears in the above-identified patent and that said Letters Patent is hereby corrected as shown below:

In column 3, line 23, change "$CO_2$" to -- $CO_3$ --.
In column 3, line 30, change "which under" to -- which, under --.

Signed and Sealed this

Fifth Day of September, 2000

Attest:

Q. TODD DICKINSON

*Attesting Officer*  *Director of Patents and Trademarks*